United States Patent [19]

Moser et al.

[11] 3,959,326

[45] May 25, 1976

[54] NICKEL STABILIZERS FOR SYNTHETIC POLYMERS

[75] Inventors: Paul Moser, Riehen; Jean Rody, Basel, both of Switzerland

[73] Assignee: Ciba-Geigy Corporation, Ardsley, N.Y.

[22] Filed: Nov. 18, 1974

[21] Appl. No.: 524,685

[30] Foreign Application Priority Data

Nov. 27, 1973 Switzerland.................... 16632/73

[52] U.S. Cl..................... 260/439 R; 260/45.75 N; 260/414
[51] Int. Cl.$^2$........................................ C07F 15/04
[58] Field of Search....................... 260/439 R, 414

[56] References Cited

UNITED STATES PATENTS

| | | | |
|---|---|---|---|
| 3,310,575 | 3/1967 | Spivack.............................. | 260/429 |
| 3,321,502 | 5/1967 | Soeder............................ | 260/439 R |
| 3,538,142 | 11/1970 | Drinkard et al............. | 260/439 R X |
| 3,660,444 | 5/1972 | Kartschmaroff et al. ........ | 260/439 R |
| 3,660,446 | 5/1972 | Carriel et al................... | 260/439 R |
| 3,661,843 | 5/1972 | Hechenbleikner et al.. | 260/439 R X |
| 3,696,135 | 10/1972 | Kartschmaroff et al. ........ | 260/439 R |
| 3,821,142 | 6/1974 | Dix et al.................. | 260/45.75 N X |

FOREIGN PATENTS OR APPLICATIONS

| | | | |
|---|---|---|---|
| 991,353 | 5/1965 | United Kingdom.......... | 260/45.75 N |
| 1,033,258 | 6/1966 | United Kingdom.......... | 260/45.75 N |

*Primary Examiner*—Helen M. S. Sneed
*Attorney, Agent, or Firm*—Charles W. Vanecek

[57] ABSTRACT

Compounds of the formula (I)

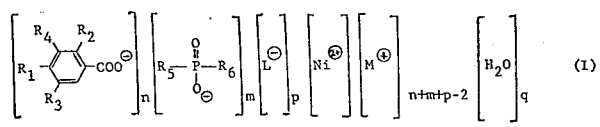

wherein either $R_1$ represents a hydroxy group and $R_2$ represents hydrogen or $R_1$ represents hydrogen and $R_2$ represents a hydroxy group, each of $R_3$ and $R_4$ independently represents hydrogen or alkyl, $R_5$ represents alkyl, cycloalkyl, aralkyl, aryl, aralkyl or aryl groups which are monosubstituted, disubstituted or trisubstituted by hydroxy, alkyl, chlorine and/or alkoxy groups, or represents alkoxy, cycloalkoxy, aralkoxy, aryloxy or aralkoxy or aryloxy which is monosubstituted or disubstituted in the aryl moiety by alkyl, chlorine and/or alkoxy, $R_6$ represents hydrogen, alkyl, cycloalkyl, aralkyl, aryl, aralkyl or aryl groups which are monosubstituted, disubstituted or trisubstituted by hydroxy, alkyl, chlorine and/or alkoxy groups, or represents alkoxy, cycloalkoxy, aralkoxy, aryloxy or aralkoxy or aryloxy which is monosubstituted or disubstituted in the aryl moiety by alkyl, chlorine and/or alkoxy groups, L is the monovalent anion of a carboxylic acid, $M^+$ is an alkali metal ion, $n$ and $m$ are 1 to 2, $p$ is 0, or 1 to 2, and $q$ is 0 to 2 are suitable for stabilizing polymer substrates.

4 Claims, No Drawings

NICKEL STABILIZERS FOR SYNTHETIC POLYMERS

The invention provides novel nickel complexes of hydroxybenzoic acids, a process for their manufacture and a method of using them as light stabilisers and/or as dye receivers for polymer substrates and also, as industrial product, the polymers that contain the claimed compounds.

The novel compounds have the formula I

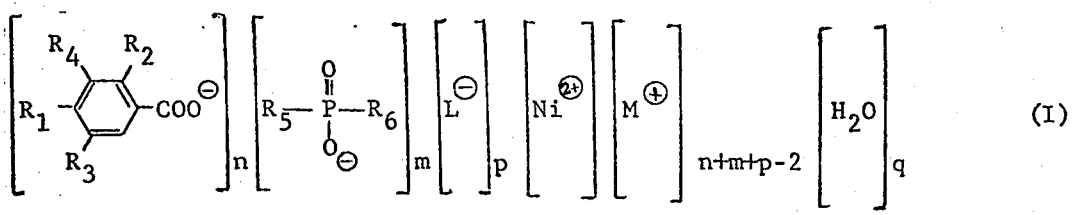

wherein either $R_1$ represents a hydroxy group and $R_2$ represents hydrogen or $R_1$ represents hydrogen and $R_2$ represents a hydroxy group, each of $R_3$ and $R_4$ independently represents hydrogen or alkyl, $R_5$ represents alkyl, cycloalkyl, aralkyl, aryl, aralkyl or aryl groups which are monosubstituted, disubstituted or trisubstituted by hydroxy, alkyl, chlorine and/or alkoxy groups, or represents alkoxy, cycloalkoxy, aralkoxy, aryloxy or aralkoxy or aryloxy which is monosubstituted or disubstituted in the aryl moiety by alkyl, chlorine and/or alkoxy, $R_6$ represents hydrogen, alkyl, cycloalkyl, aralkyl, aryl, aralkyl or aryl groups which are monosubstituted, disubstituted or trisubstituted by hydroxy, alkyl, chlorine and/or alkoxy groups, or represents alkoxy, cycloalkoxy, aralkoxy, aryloxy, or aralkoxy or aryloxy which is monosubstituted or disubstituted in the aryl moiety by alkyl, chlorine and/or alkoxy groups, L is the monovalent anion of a carboxylic acid, $M^+$ is an alkali metal ion, $n$ and $m$ are 1 to 2, $p$ is 0, or 1 to 2, and $q$ is 0 to 2.

Preferred compounds of the formula I are those wherein $R_1$ represents a hydroxy group, $R_2$ represents hydrogen, each of $R_3$ and $R_4$ independently represents hydrogen or alkyl with 1 to 5 carbon atoms, $R_5$ represents alkyl with 1 to 18 carbon atoms, cyclohexyl, aralkyl with 7 to 11 carbon atoms, aryl with 6 to 10 carbon atoms, aralkyl or aryl groups which are mono-, di- or trisubstituted by hydroxy, alkyl with 1 to 4 carbon atoms, chlorine and/or alkoxy groups with 1 to 4 carbon atoms, the aralkyl and aryl moiety containing 7 to 11 and 6 to 10 carbon atoms respectively, alkoxy with 1 to 12 carbon atoms, cyclohexoxy, aralkoxy with 7 to 11 carbon atoms, aryloxy with 6 to 10 carbon atoms, or represents aralkoxy or aryloxy which is substituted in the aryl moiety by methyl, chlorine and/or methoxy, the aralkoxy and the aryloxy moiety containing 7 to 11 and 6 to 10 carbon atoms respectively, $R_6$ represents hydrogen, alkyl with 1 to 18 carbon atoms, cyclohexyl, aralkyl with 7 to 11 carbon atoms, aryl with 6 to 10 carbon atoms, aralkyl or aryl which is mono-, di- or trisubstituted by hydroxy, alkyl with 1 to 4 carbon atoms, chlorine and/or alkoxy groups with 1 to 4 carbon atoms, the aralkyl and the aryl moiety containing 7 to 11 and 6 to 10 carbon atoms respectively, alkoxy with 1 to 12 carbon atoms, cyclohexoxy, aralkoxy with 7 to 11 carbon atoms, aryloxy with 6 to 10 carbon atoms, or represents aralkoxy or aryloxy which is substituted in the aryl moiety by methyl, chlorine and/or methoxy, the aralkoxy and the aryloxy moiety containing 7 to 11 and 6 to 10 carbon atoms respectively, L is the anion of an aliphatic carboxylic acid with 2 to 18 carbon atoms and $M^+$ is a sodium or potassium ion.

The most preferred compounds of the formula I are those wherein $R_3$ and $R_4$ represent tert. butyl, $R_5$ represents alkyl with 2 to 12 carbon atoms, cyclo-hexyl, benzyl, phenyl, benzyl or phenyl which is substituted by hydroxy and tert. butyl, or represents alkoxy with 1 to 8 carbon atoms, $R_6$ represents hydrogen, alkyl with 2 to 12 carbon atoms, cyclohexyl, phenyl, or alkoxy with 2 to 8 carbon atoms, L is the anion of acetic acid or the anion of 2-ethyl-capronic acid.

Among the most preferred compounds of the formula I, those wherein $R_5$ represents dodecyl, butoxy, phenyl or benzyl which is substituted by hydroxy and tert. butyl, $R_6$ represents hydrogen or alkoxy with 2 to 4 carbon atoms, L is the anion of ethylcapronic acid, $M^+$ is the sodium anion, $n$ and $m$ are 1, $p$ is 0 and $q$ is 0 to 1.5, have a particularly interesting utility.

If $R_3$, $R_5$ or $R_6$ represent alkyl groups these can be linear or branched alkyl groups, for example methyl, ethyl, propyl, isopropyl, n-butyl, n-hexyl, n-octyl, 2-ethylhexyl, n-dodecyl or n-octadecyl. If $R_5$ or $R_6$ represents aralkyl or substituted aralkyl groups, such groups can be, for example, benzyl, 4-methylbenzyl, 4-isopropylbenzyl, 3-chlorobenzyl, 4-methoxybenzyl, 4-hydroxy-3,5-di- tert. butylbenzyl, 2,4-dichlorobenzyl, 2-chloro-4-methylbenzyl, 1- or 2-naphthylmethyl, phenylethyl or 2-naphthylethyl. Where $R_5$ or $R_6$ represent aryl or substituted aryl groups, these can be, for example, phenyl, diphenylyl, naphtyl, 4-methylphenyl, 3-chlorophenyl, 3,4-dichlorophenyl, 4-methoxynapht-hyl-1, 4-butoxyphenyl, 3-chloro-4-methylphenyl or 3-ethoxyphenyl.

Where $R_5$ or $R_6$ represents cycloalkyl groups these can be, for example, cyclopentyl or cyclohexyl. If $R_5$ or $R_6$ represents an alkoxy or a cycloalkoxy radical, such radicals can be, for example, a methoxy, an ethoxy, isopropoxy, a butoxy, hexoxy, 2-ethylhexoxy, or a cyclohexoxy radical. $R_5$ or $R_6$ in the significance of aralkoxy or substituted aralkoxy can be, for example, a benzoxy, 4-chlorobenzoxy, 2,4-dichlorobenzoxy, 3-methylbenzoxy or 2-phenylethoxy radical. $R_5$ or $R_6$ in the significance of aryloxy or substituted aryloxy can be, for example, a phenoxy, 4-chlorophenoxy, 4-tert. butylphenoxy, 4-tert. octylphenoxy, 1- or 2-naphthoxy, 4-methoxyphenyloxy group.

According to definition, $L^-$ is the monovalent anion of an aliphatic carboxylic acid. The carboxylic acids can be unsaturated and carry substituents, for example ether or ester groups. Examples of suitable carboxylic acids are: acetic acid, glycolic acid, diglycolic acid monohexyl ester, lactic acid, 2-ethylcapronic acid, maleic acid monohexyl ester, thiodiglycolic acid monododecyl ester, lauric acid, oleic acid or stearic acid.

Where $M^+$ represents an alkali metal cation, it can be $Na^+$, $K^+$, $Li^+$, $Rb^+$ or $Cs^+$. The water content expressed in the formula by [H$_2$O]q is usually attributable to a water content of the metal salts used as starting material. Depending on the isolation and drying conditions, this water can occur partially as ligand of the central atom M$^+$, but can also be partially deposited in the end product as water of crystallisation. For this reason, the coefficient $q$ can have both the value of a whole number and of a fraction within the indicated limits.

The compounds of the formula I are, as single compounds or as mixtures, outstanding stabilisers for polymers against light-induced degradation and good receivers for chelatable dyes.

It was already known in the art to stabilise polyolefins with simple nickel benzoates. However, the novel nickel complexes surprisingly have a better heat stability compared with these salts. They can therefore be processed at elevated temperature without the polyolefins being discoloured as happens with the nickel benzoates of the prior art.

In addition, the novel nickel complexes, despite a lower nickel content, have a more pronounced light stability as compared with the nickel benzoates of the prior art. Primarily, however, they are superior to the known nickel benzoates in the sector of stabilising polyethylene, since the compounds according to the invention of the formula I dissolve readily in this substrate and have no tendency to exude.

Complexes of nickel with thiobisphenols and amines have furthermore also become known as stabilisers for polyolefins. Compared with these compounds, the novel nickel complexes of the formula I exhibit a substantially improved light stability.

As polymer substrates which can be protected from degradation by the nickel complexes of the formula I there may be mentioned principally poly-α-olefins, e.g. polyethylene, cross-linked polyethylene, polypropylene, polyisobutylene, polymethylbutene-1, polymethylpentene-1, polybutene-1, polyisoprene, polybutadiene; also polystyrene and copolymers thereof. e.g. polyacrylonitrile-styrene copolymers or poly acrylonitrile-butadiene-styrene copolymers; copolymers of olefins, e.g. ethylene-propylene copolymers, propylenebutene-1 copolymers, and terpolymers of ethylene and propylene with a diene, e.g. hexadiene, diclopentadiene or ethylidenenorbornene; mixtures of the above cited homopolymers, e.g. mixtures of polypropylene and polyethylene, polypropylene and polybutene-1, polypropylene and polyisobutylene. Polypropylene and mixtures thereof and the copolymers which contain propylene units and polyethylene are preferred.

The compounds of the formula I are incorporated into the substrates in a concentration of 0.01 to 5 percent by weight, based on the weight of the material to be stabilised. Preferably 0.05 to 1.5, but most preferably 0.1 to 0.8 percent by weight of the compounds, based on the weight of the material to be stabilised, is incorporated therein.

The incorporation can be effected after the polymerisation by blending at least one of the compounds of the formula I and optionally further additives into the melt by methods conventionally used in the art, either before or during the moulding, or also by applying the dissolved or dispersed compounds to the polymer, optionally with subsequent evaporation of the solvent.

The compounds of the formula I can also be incorporated into the polymer to be stabilised in the form of a master batch which contains the nickel stabiliser e.g. in a concentration of 2.5 to 25 percent by weight.

In the case of cross-linked polyethylene, the compounds are added before the cross-linking. Examples of further additives together with which it is possible to use the stabilisers are:

1. Antioxidants
   1.1 Simple 2,6-dialkylphenols, e.g.
      2,6-di-tert.butyl-4-methylphenol, 2-tert.butyl-4,6-dimethylphenol, 2,6-di-tert.butyl-4-methoxymethylphenol, 2,6-dioctadecyl-4-methylphenol.
   1.2 Derivatives of alkylated hydroquinones, e.g.
      2,5-di-tert.butyl-hydroquinone, 2,5-di-tert.amyl-hydroquinone, 2,6-di-tert.butyl-hydroquinone, 2,5-di-tert. butyl-4-hydroxy-anisole, 3,5-di-tert.butyl-4-hydroxyanisole, tris(3,5-di-tert.butyl-4-hydroxyphenyl)phosphite, 3,5-di-tert.butyl-4-hydroxyphenyl-stearate, bis-(3,5-di-tert.butyl-4-hydroxyphenyl)-adipate.
   1.3 Hydroxylated thiodiphenyl ethers, e.g.
      2,2'-thiobis-(6-tert.butyl-4-methylphenol), 2,2'-thiobis(4-octylphenol), 4,4'-thiobis-(6-tert.butyl-3-methylphenol), 4,4'-thiobis-(3,6-di-sec.amylphenol), 4,4'-thiobis-( 6-tert.butyl-2-methylphenol), 4,4'bis-(2,6-dimethyl-4-hydroxyphenyl)-disulphide.
   1.4 Alkylidene-bisphenols, e.g.
      2,2'-methylenebis-(6-tert.butyl-4-methylphenol),2-,2'-methylenebis-(6-tert.butyl-4-ethylphenol), 4,4'-methylenebis-(6-tert.butyl-2-methylphenol), 4,4-methylenebis-(2,6-di-tert.butylphenol), 2,6-di-(3-tert.butyl-5-methyl-2-hydroxybenzyl)-4-methylphenol, 2,2'-methylenebis-[4-methyl-6-(α-methylcyclohexyl)-phenol], 1,1-bis-(3,5-dimethyl-2-hydroxyphenyl)butane, 1,1-bis-(5-tert.butyl-4-hydroxy-2-methylphenyl)-butane, 2,2-bis-(5-tert.butyl-4-hydroxy-2-methylphenyl)-butane, 2,2-bis-(3,5-di-tert.butyl-4-hydroxyphenyl)-propane, 1,1,3-tris-(5-tert.butyl-4-hydroxy-2-methylphenyl)-butane, 2,2-bis-(5-tert.butyl-4-hydroxy-2-methylphenyl)-4-n-dodecylmercapto-butane, 1,1,5,5-tetra-(5-tert.butyl-4-hydroxy-2-methylphenyl)-pentane, ethyleneglycol-bis-[3,3-bis-(3'-tert.butyl-4'-hydroxyphenyl)-butyrate].
   1.5 O-, N- and S-benzyl compounds, e.g.
      3,5,3',5'-tetra-tert.butyl-4,4'-dihydroxydibenzyl ether, 4-hydroxy-3,5-dimethylbenzyl-thioacetic acid-octadecyl ester, tri-(3,5-di-tert.butyl-4-hydroxybenzyl)-amine, bis-(4-tert.butyl-3-hydroxy-2,6-dimethylbenzyl)dithiolterephthalate.
   1.6 Hydroxybenzylated malonic esters, e.g.
      2,2-bis-(3,5-di-tert.butyl-2-hydroxybenzyl)-malonic acid dioctadecyl ester, 2-(3-tert.butyl-4-hydroxy-5-methylbenzyl)-malonic acid dioctadecyl ester, 2,2-bis-(3,5-ditert.butyl-4-hydroxybenzyl)-malonic acid di-dodecylthioethyl ester, 2,2-bis-(3,5-di-tert.butyl-4-hydroxybenzyl) malonic acid di-[4-(1,1,3,3-tetramethylbutyl)-phenyl]-ester.
   1.7 Hydroxybenzyl aromatic compounds, e.g.
      1,3,5-tri-(3,5-di-tert.butyl-4-hydroxybenzyl)-2,4,6-trimethylbenzene, 1,4-di-(3,5-di-tert.butyl-4-hydroxybenzyl)-2,3,5,6-tetramethylbenzene, 2,4,6-tri-(3,5-di-tert.butyl-4-hydroxybenzyl)-phenol.
   1.8 s-triazine compounds, e.g.
      2,4-bis-octylmercapto-6-(3,5-di-tert.butyl-4-hydroxyanilino)-s-triazine, 2-octylmercapto-4,6-bis-(3,5-di-tert.butyl-4-hydroxy-anilino)-s-triazine, 2-octylthio-4,6-bis-(3,5-di-tert.butyl-4-hydroxyphenoxy)-s-triazine 2,4,6-tris-(3,5-di-tert.butyl-4- hydroxyphenoxy)-s-triazine, 2,4,6-tris-(3,5-di-tert-butyl-4-hydroxyphenylethyl)-s-triazine, 1,3,5-tris-(3,5-di-tert.butyl-4-hydroxybenzyl)-isocyanurate.

1.9 Amides of β-(3,5-di-tert.butyl-4-hydroxyphenyl)-propionic acid, e.g.
1,3,5-tris-(3,5-di-tert.butyl-4-hydroxyphenyl-propionyl)hexahydro-s-triazine, N,N'-di-(3,5-di-tert-butyl-4-hydroxy-phenyl-propionyl)-hexamethylenediamine.

1.10 Esters of β-(3,5-di-tert.butyl-4-hydroxyphenyl)-propionic acid.
with monohydric or polyhydric alcohols, e.g. with methanol, ethanol, octadecanol, 1,6-hexanediol, 1,9-nonanediol, ethyleneglycol, 1,2-propanediol, diethylene glycol, thiodiethyleneglycol, neopentylglycol, pentaerythritol, 3-thia-undecanol, 3-thia-pentadecanol, trimethyl-hexanediol, trimethylolethane, trimethylolpropane, tris-hydroxyethylisocyanurate, 4-hydroxymethyl-1-phospha-2,6,7-trioxabicyclo[2,2,2-]-octane.

1.11 Esters of β-(5-tert.butyl-4-hydroxy-3-methylphenyl-propionic acid
with monohydric or polyhydric alcohols, e.g. with methanol, ethanol, octadecanol, 1,6-hexanediol, 1,9-nonanediol, ethyleneglycol, 1,2-propanediol, diethyleneglycol, thiodiethyleneglycol, neopentylglycol, pentaerythritol, 3-thia-undecanol, 3-thia-pentadecanol, trimethylhexanediol, trimethylolethane, trimethylolpropane, trishydroxyethylisocyanurate, 4-hydroxymethyl-1-phospha-2,6,7-trioxabicyclo[2,2,2]octane.

1.12. Esters of 3,5-di-tert.butyl-4-hydroxyphenylacetic acid
with monohydric or polyhydric alcohols, e.g. with methanol, ethanol, octadecanol, 1,6-hexanediol, 1,9-nonanediol, ethyleneglycol, 1,2-propanediol, diethyleneglycol, thiodiethyleneglycol, neopentylglycol, pentaerythritol, 3-thia-undecanol, 3-thia-pentadecanol, trimethylhexanediol, trimethylolethane, trimethylolpropane, tris-hydroxyethylisocyanurate, 4-hydroxymethyl-1-phospha-2,6,7-trioxabicyclo[2,2,2]-octane.

1.13 Acylaminophenols, e.g.
N-(3,5-di-tert.butyl-4-hydroxyphenyl)-stearic acid amide, N,N'-di-(3,5-di-tert.butyl-4-hydroxyphenyl)-thiobisacetamide.

1.14 Benzylphosphonates, e.g.
3,5-di-tert.butyl-4-hydroxybenzyl-phosphonic acid dimethylester, 3,5-di-tert.butyl-4-hydroxybenzyl-phosphonic acid diethylester, 3,5-di-tert.butyl-4-hydroxybenzyl-phosphonic acid dioctadecyl ester, 5-tert.butyl-4-hydroxy-3-methylbenzyl-phosphonic acid dioctadecyl ester.

1.15 Aminoaryl derivatives, e.g.
phenyl-1phenyl-2-naphthylamine, N,N'-di-phenyl-p-phenylenediamine, N,N'-di-2-naphthyl-p-phenylene diamine, N,N'-di-2-naphthyl-p-phenylenediamine, N,N'-di-sec. butyl-p-phenylenediamine, 6-ethoxy-2,2,4-trimethyl-1,2-dihydroquinoline, 6-dodecyl-2,2,4-trimethyl-1,2-dihydroquinoline, mono- and dioctyliminodibenzyl, polymerised 2,2,4-trimethyl-1,2-dihydroquinoline.

2. Ultraviolet absorbers and light stability agents e.g.
2.1 2-(2'-hydroxyphenyl)-benztriazoles, for example the 5'-methyl-, 3', 5'-di-tert.butyl-, 5'-tert.butyl-, 5'-(1,1,3,3-tetramethylbutyl)-, 5-chloro-3',5'-di-tert-butyl-, 5-chloro-3'-tert.butyl-5'-methyl-, 3'-sec.butyl-5'-tert.butyl-, 3'-α-methylbenzyl-5'-methyl-,3'-α-methylbenzyl-5'-methyl-5-chloro-, 4'-hydroxy-, 4'-methoxy-, 4'-octoxy-,3',5'-di-tert.amyl, 3'-methyl-5'-carbomethoxyethyl-, 5-chloro-3',5'-di-tert.amyl derivative.

2.2 2,4-bis-(2'-hydroxyphenyl)-6-alkyl-s-triazines, e.g. the 6-ethyl or 6-undecyl derivative, 2.3 2-hydroxy-benzophenones, e.g. the 4-hydroxy, 4-methoxy, 4-octoxy, 4-decyloxy, 4-dodecyloxy, 4,2',4'-tri-hydroxy or 2'-hydroxy 4,4'-dimethoxy derivative, 2.4 1,3-bis-(2'-hydroxy-benzoyl)-benzenes, e.g.
1,3-bis-(2'-hydroxy-4'-hexyloxy-benzoyl)-benzene,
1,3-bis-(2'-hydroxy-4'-octoxy-benzoyl)-benzene,
1,3-bis-(2'-hydroxy-4'-dodecyloxy-benzoyl)-benzene.

2.5 Esters of optionally substituted benzoic acids,
e.g.: phenylsalicylate, octylphenylsalicylate, dibenzoyl-resorcinol, benzoyl-resorcinol, 3,5-di-tert.butyl-4-hydrobenzoic acid-2,4-di-tert.butyl-phenyl or -octadecyl ester, or -2-methyl-4,6-di-tert.butylphenyl ester.

2.6 Acrylates, e.g.
α-cyano-β,β-diphenylacrylic acid ethyl and isooctyl ester, α-carbomethoxy-cinnamic acid methyl ester, α-cyano-β-methyl-p-methoxy-cinnamic acid methyl and butyl ester, N-(β-carbomethoxy-vinyl)-2-methylindoline.

2.7 Sterically hindered amines, e.g.
4-benzoyloxy-2,2,6,6-tetramethylpiperidine, 4-steraroyloxy-2,2,6,6-tetramethylpiperidine, bis-(2,2,6,6-tetramethylpiperidyl)-sebacate, 3-n-octyl-7,7,9,9-tetramethyl-1,3,8-triza-spiro[4.5]decane-2,4-dione.

2.8 Oxalic acid diamides, e.g. 4,4'-di-octyloxy-oxanilide, 2,2'-di-octyloxy-5,5'-di-tert.butyl-oxanilide 2,2'-di-dodecyloxy-5,5'-di-tert. butyl-oxanilide, 2-ethoxy-2'-ethyl-oxanilide, N,N'-bis(3-dimethylaminoprophyl)-oxalamide, 2-ethoxy-5-tert.butyl-2'-ethyl-oxanilide and its mixtures with 2-ethoxy-2'-ethyl-5,4'-di-tert.butyl-oxanilide, mixtures of ortho- and para-methoxy as well as of o- and p-ethoxy disubstituted oxanilides.

3. Phosphites, e.g.
triphenylphosphite, diphenyl-alkylphosphites, phenyl-dialkylphosphites, tri-(nonylphenyl)-phosphite, trilaurylphosphite, trioctadecylphosphite, 3,9-di-isodecyloxy-2,4,8,10-tetroxa-3,9-diphospha-spiro[5,5]undecane, tri(4-hydroxy-3,5-di-tert-butylphenyl)-phosphite.

4. Compounds which decompose peroxide, e.g.
esters of β-thiodipropionic acid, for example lauryl, stearyl, myrystyl or tridecyl ester, salts of 2-mercaptobenzimidazoles, for example the zinc salt, and diphenyl thiourea.

5. Basic co-stabilisers, e.g.
melamine, benzoguanamine, polyvinylpyrrolidone, dicyandiamide, triallyl-cyanurate, urea derivatives, hydrazine derivatives, amines, polyamides, polyurethanes, alkali salts and alkaline earth salts of higher fatty acids, e.g. calcium stearate, zinc stearate, magnesium stearate, sodium ricinolate or potassium palmitate.

6. Nucleination agents, e.g.
4-tert.nutylbenzoic acid, adipic acid, diphenylacetic acid.

7. Other additives, e.g.

plasticisers, lubricants, emulsifiers, fillers, carbon black, asbestos, china clay, talcum, glass fibres, pigments, flame-proofing agents, antistatic agents.

The compounds of the formula (I) can ordinarily be manufactured by reaction of a mixture of the alkali salts of the formulae (II) and (III)

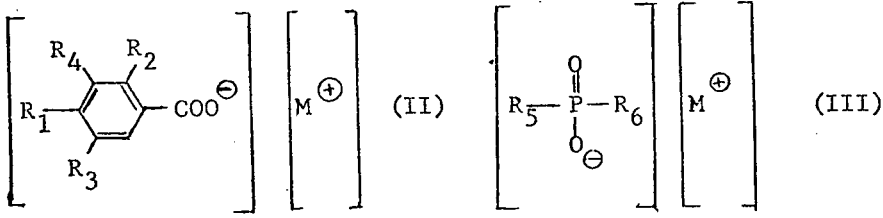

with a nickel of the formula (IV)

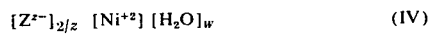

in a solvent in the ratio (II): (III): (IV) = $n : m : 1$. The symbols $R_1$ to $R_6$ and $M^{115\ 1}$ in the formulae II to IV as well as n and m have the same meanings as assigned to them in the formula I. $Z^{z-}$ represents any inorganic or organic anion of the charge z- the nickel salt of the formula IV is soluble in the reaction medium. The symbol w can have a value from 0 to 6.

The manufacture of the free acids corresponding to the alkali salts of the formula II is described in U.S. Patent No. 3.189.690. The alkali salts can be used as such or they can be manufactures direct by neutralisation of the respective acids in the reaction medium. This also applies to the alkali salts of the formula III the free acids of which are obtained by known processes, for example as described in Houben-Weyl, vol. 12/1, pp 220 ff, 294 ff, and 408 ff and vol. 12/2, pp. 5 ff and 226 ff.

Examples of suitable solvents for this reaction are water, alcohols, especially methanol, ethanol and isopropanol, ethylene glycol momoalkyl ether, dioxan, dimethyl sulphoxide and the mixtures thereof.

Examples of suitable metal salts of the formula IV are nickle chloride hexahydrate, nickel chloride dihydrate, nickel bromide, nickel sulphate hexahydrate, nickel acetate tetrahydrate, nickel stearate and the nickel salt of 2-ethylcapronic acid.

The reaction takes place by heating the reaction mixture for several hours to about 30°–130°C. However, in certain cases it is only necessary to thoroughly mix the components in one of the cited solvents. Since these manufacturing processes consist in general of equilibrium reactions, the resultant compounds of the formula I frequently occur as mixtures the compositions of which differs in accordance with different values for $n$, $m$, $p$ and $q$.

However, the compounds of the formula I can also be manufactured from the free acids corresponding to the alkali salts of the formulae II and III by reacting one equivalent of each of these acids with, for example, one equivalent of a nickel salt suspended in a solvent, e.g. nickel carbonate, or nickel bicarbonate, or freshly precipitated nickel hydroxide. This method of manufacture is particularly suitable when these free acids exhibit sufficiently strong acid reaction and when compounds of the formula I are to be manufactured for which $n=m=1$.

Examples of suitable solvents for this method of manufacture are water and organic solvents, e.g. ethers, for example dioxane, ethylene glycol monomethyl ether or mixtures of water with alcohols (especially ethanol and isopropanol). The reaction takes place advantageously by heating the reaction mixture for several hours under reflux.

The isolation of the complexes of the formula I depend on their sulubility and on the solubility of the alkali salt [$M^+$] [$Z^-$] optionally formed during the reaction in the solvent employed. If the complex is insoluble therein, it can be isolated by filtration. If the alkali salt is insoluble, it is filtered off and the complex is obtained by evaporating the solvent. If both components are insoluble, then the solvent is evaporated and the complex is isolated by extraction with a solvent of low polarity in which the alkali salt is insoluble. Examples of such solvents suitable for this purpose are diethyl ether, methylene chloride, chloroform, benzene, toluene or hexane.

If the anion [$Z^-$] has a sufficiently high coordination capacity, it can be incorporated as ligand $L^-$ into the metal complex of the formula I. As counterion, the alkali cation [$M^+$] can then become a constituent of the complex. When this happens, no alkali salt is isolated as in the processing described hereinbefore, since this has then become a constituent of the soluble complex.

The products which in the course of these isolation procedures are in many cases not obtained in pure form, but as mixtures of complexes of the formula I, are just as suitable for stabilising polymers as the homogeneous complexes.

The following Examples describe the manufacture and use of the compounds of the formula I in more detail. Parts and percentages are by weight.

EXAMPLES 1–3

27.2 g (0.1 mole) of sodium-3,5-di-tert.butyl-4-hydroxybenzoate and 0.1 mole of the sodium salt of column 2 of Table I are dissolved in the amount of water specified in column 3. To this solution are then added dropwise at room temperature 1.03 moles of the aqueous nickel salt solutions the composition of which is indicated in column 4 of Table I. The precipitate that forms is washed with water, dried at 80°C and a pressure of 11 mm Hg for 5 hours and subsequently extracted at room temperature with the extraction agent listed in column 5 of the table. The extract, which is evaporated to dryness, is dried at 80°C and a pressure of 11 mm Hg for 16 hours.

By carrying out the above procedure there are obtained the nickel complexes of column 6 of the table. The analytical data and properties of these products are listed in columns 7 to 10.

TABLE I

| 1 Example | 2 Na-salt of the ligand | 3 Water in ml as solvent | 4 Ni-salt in ml water | 5 Extraction agent | 6 Ni-complex of the composition X=3,5-di-tert.butyl-4-hydroxybenzoate | 7 Content in % of Ni | 8 P | 9 Solubilities: (h) in boiling heat (k) at room temperature | 10 Colour |
|---|---|---|---|---|---|---|---|---|---|
| 1 | $C_{12}H_{25}\overset{O}{\underset{ONa}{P}}OC_2H_5$ | 800 | Ni-acetate 4 H$_2$O (100) | benzene | NiXY . 3/4 H$_2$O<br>Y=O—ethyl-dodecyl-phosphonate | 9.75 | 4.95 | ethanol (k)<br>ligroin (k) | light yellow |
| 2 | $HO-\underset{C(CH_3)_3}{\overset{C(CH_3)_3}{\bigcirc}}-\overset{O}{\underset{H}{P}}-ONa$ | 130 | Ni-acetate 4 H$_2$O (100) | benzene | mixture of different complexes Ni$^{+2}$ with the ligands X,Y,H$_2$O Y=anion of 3,5-di-tert.butyl-4-hydroxy-phenylphosphorous acid | 9.2 | 4.5 | ethanol (k) toluene (k) ligroin (h) | green |
| 3 | $HO-\underset{C(CH_3)_3}{\overset{C(CH_3)_3}{\bigcirc}}-CH_2-\overset{O}{\underset{OC_2H_5}{P}}-ONa$ | 500 | NiCl$_2$.6H$_2$O (50) | hexane | NiXY . 1 1/2 H$_2$O Y=O—ethyl -3,5-di-tert.butyl-4-hydroxybenzylphosphonate | 8.9 | 4.4 | ethanol (k) ether (k) hexan (K) | beige |

EXAMPLE 4

27.2 g (0.1 mole) of sodium-3,5-di-tert.butyl-4-hydroxybenzoate and 16.0 g (0.1 mole of the monosodium salt of O-n-butyl-phosphorous acid are dissolved in 500 ml of ethanol. To this solution is then added a solution of 17.5 g (0.1 mole) of nickel chloride hydrate in 350 ml of ethanol. The resultant suspension is then heated for 15 minutes under reflux and the precipitated sodium chloride is filtered off. The filtrate is evaporated to dryness and the residue is extracted with methylene chloride at room temperature. After the solvent has been evaporated off, the extract is dried for 16 hours at 80°C and a pressure of 11 mm Hg to yield a compound of the composition:
NiXY
X = 3,5-di-tert-butyl-4-hydroxybenzoate ion
Y = anion of O-n-butyl-phosphorous acid.

The product is a yellowish green powder that contains 13.0% nickel and 6.7% phosphorus. It is soluble at room temperature in ethanol and toluene.

EXAMPLE 5

By proceeding in the same manner as in Example 4 it is possible to obtain from sodium-3,5-di-tert.butyl-4-hydroxybenzoate and the sodium salt of O-n-dodecylphosphorous acid a compound of the following composition:
NiXY . H$_2$O
X = 3,5-di-tert.butyl-4-hydroxybenzoate ion and
Y = anion of O-n-dodecylphosphorous acid.

The product is a yellowish green powder that contains 10.2% nickel and 5.7% phosphorus. It is soluble at room temperature in ethanol, toluene and ligroin.

EXAMPLE 6

By proceeding as described in Example 4, it is possible to obtain from sodium-3,5-di-tert.butyl-4-hydroxybenzoate and the sodium salt of O,O-di-n-butyl-phosphorous acid a compound of the composition:
NiXY . 1H$_2$O
X = 3,5-di-tert.butyl-4-hydroxybenzoate ion
Y = anion of O,O-di-n-butylphosphorous acid.

The only variation in the above process is that extraction is performed with hexane instead of methylene chloride and that the process is carried out with the application of heat.

The product is a brownish yellow powder that contains 11.4% nickel and 5.8% phosphorous. It is soluble at room temperature in ethanol, toluene and ligroin.

EXAMPLE 7

27.2 g (0.1 mole) of sodium-3,5-di-tert.butyl-4-hydroxybenzoate and 32.0 g (0.2 mole) of the sodium salt of O-n-butylphosphorous acid are dissolved in 700 ml of ethanol. To this solution is then added a solution of 17.5 g (0.1 mole) of nickel chloride dihydrate in 350 ml of ethanol. The resultant suspension is heated for 30 minutes under reflux and the sodium chloride that precipitates is filtered off. Two thirds of the filtrate are evaporated off and the remainder is removed as an azeotrope with benzene. After the benzene has been evaporated off, the residue is extracted at room temperature with methylene chloride. The concentrated extract is dried for 16 hours at 80°C and a pressure of 11 mm Hg to yield a compound of the composition:
NiXY$_2$Na . 1½ H$_2$O
X = 3.5-di-tert.butyl-4-hydroxybenzoate ion and
Y = anion of O-n-butylphosphorous acid.

The product is a yellowish green powder that contains 9.3% nickel and 10.1% phosphorus. It is soluble at room temperature in ethanol and methylene chloride and with the application of heat in toluene.

EXAMPLE 8

By proceeding in the same manner as described in Example 7, it is possible to obtain from sodium-3,5-di-tert.butyl-4-hydroxybenzoate and the sodium salt of O-ethyl-3,5-di-tert.butyl-4-hydroxybenzylphosphonic acid a compound of the following composition:
NiXYNa . 2H$_2$O
X = 3,5-di-tert.butyl-4-hydroxybenzoate ion and
Y = anion of O-ethyl-3,5-di-tert.butyl-4-hydroxybenzyl-phosphonic acid The product is a yellowish beige powder that contains 5.8% nickel nd 6.4% phosphorus. It is soluble at room temperature in ethanol and toluene and with the application of heat in ligroin.

EXAMPLE 9

25.0 g (0.1 mole) of 3,5-di-tert.butyl-4-hydroxybenzoic acid, 32.2 g (0.1 mole) of O,O-di-n-octylphosphoric acid and 12.3 g of nickel carbonate (0.13 mole) are suspended in 500 ml of ethylene glycol dimethyl ether. This suspension is then heated under reflux until it is no longer possible to observe the escape of $CO_2$ from the reaction vessel. The reaction mixture is the clarified by filtration and evaporated to dryness. The residue is taken up in benzene and evaporated firstly under external pressure and towards the end in vacuo. This residue is dried for 16 hours at 80°C and a pressure of 11 mm Hg to yield a compound of the following composition:

NiXY . 1 $H_2O$

X = 3,5-di-tert.butyl-4-hydroxybenzoate ion and
Y = anion of O,O-di-n-octylphosphoric acid.

The product is a hard, green resin that contains 9.1% nickel and 4.9 % phosphorus. Is is soluble at room temperature in ethanol, toluene and ligroin.

EXAMPLE 10

27. g (0.1 mole) of sodium-3,5-di-tert.butyl-4-hydroxybenzoate and 29.2 g (0.1 mole) of the sodium salt of 3,5-di-tert.butyl-4-hydroxyphenylphosphorous acid are dissolved in 240 ml of ethanol. To this solution is then added at room temperature and over the course of one hour a solution of 34.5 g (0.1 mole) of nickel-2-ethylcapronate in 85 ml of ethanol. The resultant green solution is evaporated to dryness. The residue is dried for 16 hours at 80°C and a pressure of 11 mm Hg. The product is a yellowish green substance that contains 6.6% nickel and 3.2% phosphorus and is readily soluble in all organic solvents. Its composition can be described by the formula $NiXYL_2Na_2$ wherein X represents 3,5-di-tert.butyl-4-hydroxybenzoate ion, Y represents the anion of 3,5-di-tert.butyl-4-hydroxyphenylphosphorous acid, and L represents the 2-ethylcapronate ion.

EXAMPLE 11

1000 parts of polypropylene powder (melt index 1.5 g/10 minutes, 230°C) are mixed in a drum mixer with 1 part of pentaerythritol-tetrakis-[3-(3',5'-di-tert.butyl-4-hydroxyphenyl)-propionate], 3 parts of dilaurythiodipropionate (DLDTP), 5 parts of a light stability agent of Table II and, in the indicated experiments, 5 parts of cadmium yellow (yellow cadmium sulphide pigment), and the mixture is subsequently homogenised in a Brabender plastograph at 200°C over the course of 10 minutes. The polymer mass is then pressed to 1 mm thick sheets in a heated press over the course of 6 minutes at the temperatures stated in the table. A visual evaluation of the test samples in respect of their discolouration yields the following results:

TABLE II

| light stability agent | without cadmium yellow at T= | | | without cadmium yellow at T= | | |
| --- | --- | --- | --- | --- | --- | --- |
| | 260°C | 280°C | 300°C | 260°C | 280°C | 300°C |
| Nickel-3,5-di-tert-butyl-4-hydroxybenzoate | D | strong D | strong D | — | — | — |
| Compound according to Example 1 | i.o. | i.o. | D | slight D | D | D |
| 2 | D | D | D | — | — | — |
| 3 | i.o. | i.o. | i.o. | i.o. | slight D | slight D |
| 4 | i.o. | i.o. | i.o. | i.o. | i.o. | slight D |
| 5 | i.o. | i.o. | slight D | — | — | — |
| 6 | i.o. | slight D | slight D | slight D | D | D |
| 7 | i.o. | i.o. | i.o. | — | — | — |
| 8 | i.o. | i.o. | slight D | — | — | — |
| 9 | i.o. | i.o. | i.o. | — | — | — |
| 10 | D | D | D | — | — | — |

Abbreviations:
i.o. = no discolouration
D = discolouration (degree: slight D, D, strong D)

EXAMPLE 12

100 parts of polyethylene with a density of 0.917 are homogeneously mixed in a Brabender plastograph with 0.1 and 0.3 parts respectively of a light stability agent (LSA) of the formula I at 180°C over the course of 10 minutes. The resultant mass is pressed in a daylight-press at 180°C to 1 mm thick sheets which are examined visually for undissolved particles. The sheets are hung up at room temperature and examined periodically for signs of efflorescence. The results are reported in Table III.

TABLE III

| light stability agent (LSA) | solubility | | compability* | |
| --- | --- | --- | --- | --- |
| | 0,1 % LSA | 0,3 % LSA | 0,1 % LM | 0,3 % LM |
| nickel-3,5-di-tert.butyl-4-hydroxy-benzoate | not dissolved | not dissolved | — | — |
| Compound according to Example 6 | dissolved | dissolved | >70 | 50 |
| Compound according to Example 10 | dissolved | dissolved | >70 | >70 |

*compability: number of days after which no signs of efflorescence can be observed.

EXAMPLE 13

1000 parts of polypropylene powder (melt index 1.5 g/10 minutes at 230°C, 2160 g are mixed in a drum mixer with 1 part of pentaerythritol-tetrakis-[3-(3',5'-di-tert.butyl-4-hydroxyphenyl)-propionate] and 2.5 parts of a nickel compound of Table IV and subsequently granulated in an extruder at a temperature of 200°-220°. The resultant granules are processed to a sheet in the conventional manner using an extruder with slot die. This sheet is cut into ribbons which are then streched to 6 times their lenght at elevated temperature and wound on a spool. The titre of the ribbons is 700–900 den., and their ultimate tensile strenght is 5,5–6,5 g/den.

These polypropylene ribbons are applied without tension to test carriers and exposed in a xenotest apparatus 150. Five test specimens are taken after different times and their ultimate tensile determined. Criterion for the protective action of the individual nickel compounds is the "protective factor", which is defined as follows:

$$\text{"protective factor"} = \frac{\text{exposure time of the light stabilized sample up to 50\% loss of ultimate tensile strength}}{\text{exposure time of the unstabilised sample up to 50\% loss of ultimate tensile strength}}$$

The values obtained are listed in Table IV:

TABLE IV

| light stability agent | "protective factor" | exposure time up to 50% loss of ultimate tensile strength |
|---|---|---|
| none | 1,0 | 400 |
| Compound according to Example 1 | 3,5 | 1400 |
| Compound according to Example 2 | 3,5 | 1420 |
| Compound according to Example 3 | 2,6 | 1050 |
| Compound according to Example 6 | 5,0 | 2000 |
| Compound according to Example 7 | 5,0 | 2000 |
| Compound according to Example 8 | >3,5 | >1400 |
| Compound according to Example 10 | 2,3 | 940 |

We claim:
1. Compounds of the formula (I)

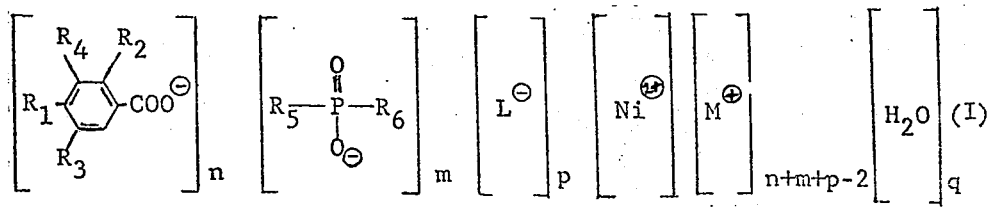

wherein either $R_1$ represents a hydroxy group and $R_2$ represents hydrogen or $R_1$ represents hydrogen and $R_2$ represents a hydroxy group, each of $R_3$ and $R_4$ independently represents hydrogen or alkyl, $R_5$ represents alkyl, cycloalkyl, aralkyl, aryl, aralkyl or aryl groups which are monosubstituted, disubstituted or trisubstituted by hydroxy, alkyl, chlorine and/or alkoxy groups, or represents alkoxy, cycloalkoxy, aralkoxy, aryloxy or aralkoxy or aryloxy which is monosubstituted or disubstituted in the aryl moiety by alkyl, chlorine and/or alkoxy, $R_6$ represents a hydrogen, alkyl, cycloalkyl, aralkyl, aryl, aralkyl or aryl groups which are monosubstituted, disubstituted or trisubstituted by hydroxy, alkyl, chlorine and/or alkoxy groups, or represents alkoxy, cycloalkoxy, aralkoxy, aryloxy or aralkoxy or aryloxy which is monosubstituted or disubstituted in the aryl moiety by alkyl, chlorine and/or alkoxy groups, L is the monovalent anion of an aliphatic carboxylic acid, $M^+$ is an alkali metal ion, $n$ and $m$ are 1 to 2, $p$ is 0, or 1 to 2, and $q$ is 0 to 2.

2. Compounds according to claim 1, wherein $R_1$ represents a hydroxy group, $R_2$ represents hydrogen, each of $R_3$ and $R_4$ independently represents hydrogen or alkyl with 1 to 5 carbon atoms, $R_5$ represents alkyl with 1 to 18 carbon atoms, cyclohexyl, aralkyl with 7 to 11 carbon atoms, aryl with 6 to 10 carbon atoms, aralkyl or aryl groups which are mono-, di- or tri-substituted by hydroxy, alkyl with 1 to 4 carbon atoms, chlorine and/or alkoxy groups with 1 to 4 carbon atoms, the aralkyl and aryl moiety containing 7 to 11 and 6 to 10 carbon atoms respectively, alkoxy with 1 to 12 carbon atoms, cyclohexyloxy, aralkoxy with 7 to 11 carbon atoms, aryloxy with 6 to 10 carbon atoms, or represents aralkoxy or aryloxy which is substituted in the aryl moiety by methyl, chlorine and/or methoxy, the aralkoxy and the aryloxy moiety containing 7 to 11 and 6 to 10 carbon atoms respectively, $R_6$ represents hydrogen, alkyl with 1 to 18 carbon atoms, cyclohexyl, aralkyl with 7 to 11 carbon atoms, aryl with 6 to 10 carbon atoms aralkyl or aryl which is mono-, di- or trisubstituted by hydroxy, alkyl with 1 to 4 carbon atoms, chlorine and/or alkoxy groups with 1 to 4 carbon atoms, the aralkyl and the aryl moiety containing 7 to 11 and 6 to 10 carbon atoms respectively, alkoxy with 1 to 12 carbon atoms, cyclohexyloxy, aralkoxy with 7 to 11 carbon atoms, aryloxy 6 to 10 carbon atoms, or represents aralkoxy or aryloxy which is substituted in the aryl moiety by methyl, chlorine and/or methoxy, the aralkoxy and the aryloxy moiety containing 7 to 11 and 6 to 10 carbon atoms respectively, L is the anion of an aliphatic carboxylic acid with 2 to 18 carbon atoms and $M^+$ is a sodium or potassium ion.

3. Compounds according to claim 2, wherein $R_3$ and $R_4$ represent tert.butyl, $R_5$ represents alkyl with 2 to 12 carbon atoms, cyclohexyl, benzyl, phenyl, benzyl or phenyl which is substituted by hydroxy and tert.butyl, or represents alkoxy with 1 to 8 carbon atoms, $R_6$ represents hydrogen, alkyl with 2 to 12 carbon atoms, cyclohexyl, phenyl, or alkoxy with 2 to 8 carbon atoms, L is the anion of acetic acid or the anion of 2-ethylcapronic acid.

4. Compounds according to claim 3, wherein $R_5$ represents dodecyl, butoxy, phenyl or benzyl which is substituted by hydroxy and tert.butyl, $R_6$ represents hydrogen or alkoxy with 2 to 4 carbon atoms, $n$ and $m$ are 1, $p$ is 0 and $q$ is 0 to 1.5.

* * * * *